United States Patent [19]

Gärtner et al.

[11] Patent Number: 4,483,802

[45] Date of Patent: Nov. 20, 1984

[54] PROCESS FOR THE PREPARATION OF SULFONATED ARYL PHOSPHINE

[75] Inventors: Roderich Gärtner; Boy Cornils, both of Dinslaken; Helmut Springer; Peter Lappe, both of Oberhausen, all of Fed. Rep. of Germany

[73] Assignee: Ruhrchemie Aktiengesekkschaft, Fed. Rep. of Germany

[21] Appl. No.: 534,089

[22] Filed: Sep. 20, 1983

[30] Foreign Application Priority Data

Sep. 22, 1982 [DE] Fed. Rep. of Germany ....... 3235030

[51] Int. Cl.$^3$ ............................................ C07C 143/24
[52] U.S. Cl. ........................ 260/505 C; 260/505 N; 260/505 P; 260/505 R
[58] Field of Search ........... 260/505 R, 505 N, 505 P, 260/505 C

[56] References Cited

U.S. PATENT DOCUMENTS 4,110,366  8/1978  Tamabayashi et al. ........ 260/505 N

FOREIGN PATENT DOCUMENTS 2627354  12/1976  Fed. Rep. of Germany .

OTHER PUBLICATIONS

J. Chem. Soc. 1958, pp. 281, 282.

*Primary Examiner*—Alan Siegel
*Attorney, Agent, or Firm*—Jordan B. Bierman

[57] ABSTRACT

A process for the preparation of mono, di or trisulfonated aryl phosphines whereby triaryl phosphine is sulfonated with oleum at 0° to 40° C. After dilution of the reaction product with water, the sulfonated triaryl phosphine is extracted with an amine dissolved in an organic solvent; both the amine and organic solvent being insoluble in water. From the organic phase the sulfonated phosphine is transferred to the aqueous phase by treatment with an aqueous solution of a base.

11 Claims, No Drawings

PROCESS FOR THE PREPARATION OF SULFONATED ARYL PHOSPHINE

This Application claims priority of German Application No. P 32 35 030.9, filed Sept. 22, 1982.

The present invention relates to a process for the preparation of pure sulfonated aryl phosphines. The preparation of sulfonated phenyl phosphines generally is known. The sodium salt of the m-sulfophenyl diphenyl phosphine, for example, is obtained by the reaction of triphenyl phosphine with oleum, heating the reaction mixture over a water bath, diluting the reaction product with water, and then neutralizing with sodium hydroxide. The desired compound is crystallized out of the mixture (J. Chem. Soc. 1958, pages 281, 282).

In a similar process, sodium salts of di(m-sulfophenyl)phenyl phosphine and tri(m-sulfophenyl) phosphine can also be obtained. The starting material is, in both cases, triphenyl phosphine, which is reacted with oleum at temperatures between 18 and 40° C. for a period of 15 to 63 hours. The reaction product is diluted with water and neutralized with sodium hydroxide. The temperature is maintained under 20° C. while the sodium hydroxide is added to the mixture (DE-PS No. 26 27 354).

The free acids are obtained by treating the sodium salts with a cation exchange resin and can then be converted to other salts with different bases. In this way the barium and tetraethylammonium salts of the tri(m-sulfophenyl) phosphine, for example, can be prepared (DE-PS No. 26 27 354).

A disadvantage of the known processes for the preparation of sulfonated aryl phosphines is the formation of numerous by-products, particularly the various sulfonation stages of aryl phosphines, aryl phosphine oxides and aryl phosphine sulfides. Pure compounds can only be obtained by costly and wasteful purification operations.

Sulfonated aryl phosphines are used, among other things, as components of catalyst systems. For these and other applications pure substances are required. They must be free of the aforesaid impurities which occur as by-products in the process of preparation, as well as those drawn into the reaction mixture in the course of the reaction, such as chloride and iron ions. Therefore, it has become imperative to develop a simple method of preparing pure sulfontated aryl phosphines which does not require repetitive purification steps.

According to the invention, this aim is achieved for the preparation of mono, di, or trisulfonated aryl phosphines by the sulfonation of aryl phosphines, preferably triaryl phosphines with oleum at 0° to 40° C. dilution of the sulfonation mixture with water. It is characterized in that the aqueous solution is extracted with a solution of an amine in an organic solvent, both the amine and organic solvent being insoluble in water.

About 0.5 to about 1.5 mol of the amine per equivalent of sulfonic acid group is used. The organic phase is then separated, stirred vigorously with an aqueous solution of a base whereby the phosphine is transferred to the aqueous portion. The aqueous solution containing the phosphine is then separated from the organic phase and the sulfonated aryl phosphine is isolated therefrom.

The new procedure makes it possible to free salts of sulfonated aryl phosphines from impurities which enter the reaction product during the manufacturing process. Furthermore, this process also allows byproducts of the various sulfonation stages to be removed, the desired aryl phosphines to be enriched, and the various aryl phosphines to be separated from each other.

A process for the separation of water-soluble salts of aromatic sulfonic acids is described in EP-A No. 00 41 134. Here a sulfonation mixture diluted in water is treated with an amount of a water-soluble amine which is equivalent to the sulfonic acid residues. The amine forms a lipophilic salt with the sulfonic acid group. The two ensuing phases are then separated and the phase containing the ammonium salt is treated with a stoichiometric amount of a water-soluble base, the sulfonic acid salt of which is to be prepared. The sulfonic acid salt is thereby obtained in an aqueous solution from which it can be isolated. This process presupposes that the ammonium salt is liquid below the boiling point of the aqueous sulfuric acid. Moreover, the sulfonates to be treated according to this process must contain no by-products like phosphine oxides and phosphine sulfides which have a very similar constitution to the desired compounds and, therefore, exhibit hardly any difference in physical behavior but, nevertheless, must be completely separated therefrom.

The new process is generally applicable to mono, di or trisulfonated aryl phosphines or their mixtures; particularly phosphines having phenyl or naphthyl groups which can, in some cases, also contain alkyl groups. The sulfonic acid groups of the sulfonated aryl phosphine are distributed as evenly as possible among the aryl groups.

The process according to the invention is conducted as follows:

The appropriate arylphosphine and sulfonating agent known in the art are reacted and form a sulfonation mixture. While a temperature of between about 0° and about 90° C., preferably between about 20° and about 40° C., is maintained, the sulfonation mixture is mixed with enough water to dilute the sulfuric acid present to 0.5 to 50% by weight, preferably 25 to 35% by weight. A water-insoluble amine dissolved in a water-insoluble organic solvent is added to the diluted solution. The concentration of the amine solution is advantageously 0.5 to 35% by weight, preferably 10 to 30% by weight, and more preferably 15 to 25% by weight amine.

0.5 to 1.5 mole, preferably 0.8 to 1.2 mole amine per equivalent of sulfonic acid group is used. The use of excess amine insures that only minimal losses in yield occur. A greater excess of amine than in the process according to the invention is possible but does not lead to an improvement in the results of the separation, the purification, or the yield.

After thorough mixing, two phases are formed. The aqueous phase, which has a higher specific gravity, contains the acid, while the organic phase, which has a low sulfate content, contains the amine salt of the sulfonic acid groups dissolved in the organic solvent (salt phase). The salt phase is separated.

The salt is subsequently reacted with an aqueous solution of a base, the sulfonic acid salt of which is to be prepared. The amount of base used is chemically equivalent to the amount of amine salt dissolved. Excess base leads to impurities in the final product. By recovery of the water-insoluble amine, an aqueous solution of the desired sulfonic acid salt is obtained. The amine which remains can be reused.

The process according to the invention can be conducted either discontinuously or continuously. Conventional apparatus for material separation, such as a countercurrent extraction unit, is conveniently used. Instead of adding the base dissolved in water to the solution of the amine salt in the organic medium all at once, it can be added in parts according to a preferred procedure of the process of the invention. This procedure is used with particular success when the aim is to separate a sulfonation mixture which contains products of different sulfonation stages. The number of re-extraction steps, i.e. the transfer of the sulfonic acid dissolved as an amine salt in the organic medium into the aqueous phase by treatment with the aqueous solution of a base, must be adjusted to the composition of the reaction mixture. Generally speaking, two to five re-extractions are sufficient to obtain the pure aryl phosphine sulfonic acids.

It is expedient to continue adding the aqueous solution of base to the organic phase until a certain pH value is attained, separate the phases from each other, start adding the base again until higher pH values have been attained, and working up the aqueous solutions obtained therefrom separately.

The water-insoluble amines for use in the invention may be homo or heterocyclic, aliphatic, aromatic, or araliphatic; preferably they are open-chained, branched or unbranched aliphatic amines having 10 to 60 — more preferably 13 to 36 — carbon atoms. Amines whose salts with the sulfonic acids are insoluble in the organic solvents or only soluble to a limited extent are less suitable for the process. Particularly suitable amines are tri-n-octyl amine, tri-iso-octyl amine, tri-2-ethylhexyl amine, methyl-di-octyl amine, and tridodecyl amine.

The amines are dissolved in an organic water-insoluble solvent. Particularly suitable are aliphatic or aromatic hydrocarbons or hydrocarbon mixtures, e.g. toluene or fractions resembling kerosene as well as $C_4$-$C_{20}$ alcohols and $C_8$-$C_{20}$ ethers.

Any water soluble base, organic or inorganic, may be used for the basic aqueous solution employed to transfer the sulfonic acid phosphines to the water phase. The particular base chosen depends on the desired final salt of the sulfonated aryl phosphines. These include alkali and alkaline earth metal hydroxides, ammonia, alkali carbonates, and water soluble amines such as methyl amine, ethyl amine, propyl amine, butyl amine and ethanolamine. Alkali hydroxides are particularly useful.

It is expedient to carry out the process at room temperature. Higher temperatures bring no advantages.

The Examples which follow are designed to illustrate the invention without limiting it. The data on the solubility of the amines and the organic solvents in water are based on the temperatures at which the process is carried out. The final product is either left in the aqueous solution or is obtained in solid form by vaporization, crystallization, decantation, or filtering.

The abbreviations used mean the following:
TPPMS: triphenyl phosphine monosulfonic acid salt
DS: triphenyl phosphine disulfonic acid salt
TS: triphenyl phosphine trisulfonic acid salt
OMS: triphenyl phosphine oxide monosulfonic acid salt
ODS: triphenyl phosphine oxide disulfonic acid salt
OTS: triphenyl phosphine oxide trisulfonic acid salt
SDS: triphenyl phosphine sulfide disulfonic acid salt
STS: triphenyl phosphine sulfide trisulfonic acid salt

EXAMPLE 1

Preparation of TPPDS as well as extraction of the sulfonation mixture 960 g of 30% oleum (D=1.94) are placed in a 1 liter flask equipped with a stirrer, thermometer, dropping funnel, and cooler and cooled under a nitrogen atmosphere to an internal temperature of 15° C. Then over a period of two hours, 105 g (0.4 mole) of triphenyl phosphine and a further 320 g of 30% oleum are added with stirring, and the reaction temperature is kept between 15° and 20° C. After addition of the oleum and triphenyl phosphine has been completed, the reaction mixture is stirred for a further 3.5 hours at 20° C.

Subsequently, the contents of the flask are added under the protection of a nitrogen atmosphere to a 6 liter flask containing 2505 g of water having a temperature of about 10° C. During the addition the internal temperature is kept between 20° and 40° C. by intensive external cooling.

The composition of the reaction solution is as follows (m=3890 g):

TABLE 1

|  | Mass (g) | m Mol | Mol % |
| --- | --- | --- | --- |
| TPPMS | 2.3 | 6 | 1.5 |
| DS | 119.8 | 257 | 64.1 |
| TS | 26.5 | 44 | 11.0 |
| ODS | 26.1 | 54 | 13.5 |
| OTS | 8.6 | 15 | 3.7 |
| SDS | 8.2 | 17 | 4.2 |
| STS | 4.7 | 8 | 2.0 |

The homogenous sulfonation mixture of the above composition is placed under a nitrogen atmosphere in a 6 liter flask and stirred with a mixture of 303 g (858 mMol) of triisooctyl amine and 1212 g of toluene. After addition has been completed, the reaction mixture is stirred for a further 30 minutes and left to separate for 30 minutes. The lower phase (3665 g of aqueous sulfuric acid) is separated and discarded.

The composition of the organic phase (1731 g) is as follows:

TABLE 2

|  | Mass (g) | m Mol | Mol % |
| --- | --- | --- | --- |
| TPPMS | 2.1 | 6 | 1.5 |
| DS | 118.5 | 254 | 63.7 |
| TS | 26.8 | 44 | 11.0 |
| ODS | 27.3 | 57 | 14.3 |
| OTS | 8.9 | 15 | 3.8 |
| SDS | 7.9 | 16 | 4.0 |
| STS | 4.3 | 7 | 1.7 |

The organic phase contains 1.3% by weight of sulfate.

EXAMPLE 2

Preparation of TPPTS as well as extraction of the sulfonation mixture

As in Example 1, 960 g of 30% oleum are placed in a 1 liter flask. Over a period of 2 hours, 105 g (0.4 mol) of triphenyl phosphine and a further 320 g of 30% oleum are added. Afterwards, the mixture is stirred for a further 24 hours at 20° C.

The reaction mixture is subsequently added to 2502 g of water at 10° C. and 3887 g of sulfonation mixture with the following composition is obtained:

TABLE 3

|  | g | m Mol | Mol % |
| --- | --- | --- | --- |
| TPPDS | 62.6 | 134 | 33.8 |
| TS | 128.7 | 213 | 53.8 |
| ODS | 6.9 | 14 | 3.5 |
| OTS | 15.7 | 27 | 6.8 |

TABLE 3-continued

|  | g | m Mol | Mol % |
|---|---|---|---|
| STS | 4.7 | 8 | 2.1 |

The homogenous sulfonation mixture of the above composition is blended as in Example 1 with a mixture of 338 g (1099 mMol) of triisoctyl amine and 1552 g of toluene. After phase separation, 3660 g of an aqueous sulfuric acid solution and 2167 g of organic phase with the following composition are obtained:

TABLE 4

|  | Mass (g) | m Mol | Mol % |
|---|---|---|---|
| TPPDS | 61.7 | 132 | 34.1 |
| TS | 126.9 | 210 | 54.3 |
| ODS | 7.2 | 15 | 3.9 |
| OTS | 12.1 | 21 | 5.4 |
| STS | 5.2 | 9 | 2.3 |

The sulfate concentration in the organic phase is 1.44% by weight.

EXAMPLE 3

Re-extraction of an amine extraction solution containing TPPDS with a diluted potassium hydroxide solution at 20° C.

As in Example 1, a sulfonation mixture mainly containing TPPDS, is prepared and extracted with a solution of triisooctyl amine and toluene. The composition of the organic solution (3000 g) is as follows:

TABLE 5

|  | g | m Mol | Mol % |
|---|---|---|---|
| TPPMS | 1.6 | 4 | 0.6 |
| DS | 207.4 | 445 | 64.4 |
| TS | 46.4 | 77 | 11.1 |
| ODS | 47.3 | 98 | 14.2 |
| OTS | 15.4 | 26 | 3.8 |
| SDS | 13.7 | 28 | 4.1 |
| STS | 7.5 | 13 | 1.8 |

The sulfate concentration is 1.4% by weight.

Subsequently, the extraction product is mixed in a 6 liter flask with 5% aqueous potassium hydroxide solution with stirring and under a nitrogen atmosphere. The pH value is measured with a standard glass electrode. When the desired pH value has been reached, the addition of potassium hydroxide solution is interrupted.

The system of triisooctyl amine, toluene and the potassium salts of the sulfonated triphenyl phosphines, as well as of the corresponding oxides and sulfides, which forms two phases, is separated and the water-free organic phase is once again mixed with aqueous potassium hydroxide solution. The organic phase is either discarded or reused for the extraction of sulfonation mixtures.

The composition of the aqueous solutions of the potassium salts is listed in the following tables:

TABLE 6

| sample | ph value | mass aqueous phase (g) | DS g | DS mMol | TS g | TS mMol | ODS g | ODS mMol | OTS g | OTS mMol | SDS g | SDS mMol | STS g | STS mMol | $SO_4^{2-}$ g | $SO_4^{2-}$ mMol |
|---|---|---|---|---|---|---|---|---|---|---|---|---|---|---|---|---|
| 1 | 4.00 | 1131.3 |  |  |  |  | 1.2 | 2 |  |  |  |  |  |  | 38.5 | 400 |
| 2 | 5.00 | 195.6 |  |  | 1.5 | 2 | 16.6 | 34 | 8.1 | 14 |  |  | 0.5 | 1 | 0.8 | 8 |
| 3 | 5.25 | 154.8 |  |  | 4.0 | 7 | 13.4 | 28 | 3.9 | 7 |  |  | 0.8 | 1 | 0.2 | 2 |
| 4 | 5.50 | 102.6 | 0.4 | 1 | 9.2 | 15 | 9.5 | 20 | 1.5 | 3 |  |  | 1.1 | 2 | 0.1 | 1 |
| 5 | 5.75 | 118.5 | 0.9 | 2 | 17.9 | 30 | 4.0 | 8 | 0.4 | 1 | 0.3 | 1 | 1.6 | 3 | <0.1 |  |
| 6 | 6.00 | 78.6 | 2.4 | 5 | 9.5 | 16 | 0.8 | 2 |  |  | 0.8 | 2 | 2.2 | 4 | <0.1 |  |
| 7 | 6.25 | 189.0 | 33.2 | 71 | 3.3 | 5 | 1.1 | 2 |  |  | 2.2 | 4 | 1.2 | 2 |  |  |
| 8 | 6.50 | 427.8 | 85.9 | 184 |  |  | 2.4 | 5 |  |  | 5.7 | 11 |  |  |  |  |
| 9 | 6.75 | 211.2 | 48.4 | 104 |  |  | 1.0 | 2 |  |  | 2.9 | 6 |  |  |  |  |
| 10 | 7.00 | 60.3 | 17.9 | 38 |  |  | 0.5 | 1 |  |  | 1.2 | 2 |  |  |  |  |
| 11 | 7.50 | 40.5 | 6.6 | 14 |  |  | 0.3 | 1 |  |  | 0.7 | 1 |  |  |  |  |
| 12 | 8.15 | 27.0 | 4.5 | 10 |  |  | 0.2 |  |  |  | 0.3 | 1 |  |  |  |  |

Samples 8 and 9 exhibit a DS content of 91.3 and 92.5% by weight. By concentration of the aqueous solutions until the beginning of crystallization, followed by filtration, washing with methanol, and drying, the potassium salt of the di(m-sulfophenyl) phenyl phosphine can be obtained as a whie solid with a purity of at least 95%.

EXAMPLE 4

Re-extraction af an amine extraction solution containing TPPTS with diluted potassium hydroxide solution at 20° C.

As in Example 2, a sulfonation mixture, primarily containing TPPTS, is prepared and extracted with a toluene solution of triisooctyl amine. The composition of the organic phase thus obtained (1926 g) is as follows:

TABLE 7

|  | Mass (g) | m Mol | Mol % |
|---|---|---|---|
| TPPDS | 56.6 | 121 | 30.2 |
| TS | 131.5 | 218 | 54.5 |
| ODS | 6.8 | 14 | 3.5 |
| OTS | 16.2 | 28 | 7.0 |
| SDS | 2.1 | 4 | 1.0 |
| STS | 8.7 | 15 | 3.8 |

The sulfate concentration in the organic phase is 1.52% by weight.

Re-extraction with 5% aqueous potassium hydroxide solution is carried out as in Example 3 at an internal temperature of 20° C. The results are listed in the following table:

TABLE 8

| Sample | ph value | mass aqueous phase (g) | DS g | DS mMol | TS g | TS mMol | ODS g | ODS mMol | OTS g | OTS mMol | SDS g | SDS mMol | STS g | STS mMol | $SO_4^{2-}$ g | $SO_4^{2-}$ mMol |
|---|---|---|---|---|---|---|---|---|---|---|---|---|---|---|---|---|
| 1 | 4.02 | 618 |  |  |  |  |  |  | 2.2 | 4 |  |  |  |  | 27.4 | 285 |
| 2 | 5.00 | 80 |  |  | 3.6 | 6 | 1.7 | 4 | 5.4 | 9 |  |  | 1.2 | 2 | 1.4 | 14 |

TABLE 8-continued

| Sample | ph value | mass aqueous phase (g) | DS g | DS mMol | TS g | TS mMol | ODS g | ODS mMol | OTS g | OTS mMol | SDS g | SDS mMol | STS g | STS mMol | $SO_4^{2-}$ g | $SO_4^{2-}$ mMol |
|---|---|---|---|---|---|---|---|---|---|---|---|---|---|---|---|---|
| 3 | 5.25 | 60 | | | 7.5 | 12 | 1.5 | 3 | 2.7 | 5 | | | 1.1 | 2 | 0.2 | 2 |
| 4 | 5.50 | 142 | 0.3 | 1 | 23.6 | 39 | 0.9 | 2 | 2.0 | 3 | | | 1.8 | 3 | <0.1 | |
| 5 | 5.75 | 212 | 0.3 | 1 | 38.4 | 64 | 0.4 | 1 | 1.2 | 2 | | | 2.1 | 3 | <0.1 | |
| 6 | 6.00 | 219 | 0.7 | 11 | 39.2 | 65 | 0.3 | 1 | 1.2 | 2 | | | 1.3 | 2 | | |
| 7 | 6.25 | 96 | 6.0 | 13 | 15.7 | 26 | 0.4 | 1 | 0.4 | 1 | | | 0.4 | 1 | | |
| 8 | 6.75 | 150 | 23.1 | 50 | 4.4 | 7 | 0.4 | 1 | | | 1.1 | 2 | 0.2 | | | |
| 9 | 7.00 | 86 | 16.0 | 34 | | | 0.6 | 1 | | | 0.7 | 1 | | | | |
| 10 | 7.54 | 49 | 8.9 | 19 | | | 0.3 | 1 | | | | | | | | |

Samples 5 and 6 exhibit a TS content of 90.6 and 91.8% by weight, respectively. By concentration of the aqueous solutions until the commencement of crystallization, followed by filtration, washing with methanol, and drying, the potassium salt of the tri-(m-sulfophenyl) phosphine can be obtained as a white solid with a purity of at least 95%.

EXAMPLE 5

Influence of the amine quantity on the extraction of a sulfonation mixture containing TPPDS A sulfonation mixture prepared as in Example 1, is extracted with different amounts of triisooctyl amine and toluene in the manner indicated in Example 1.

The sulfonation mixture (432 g) exhibits the following composition:

TABLE 9

| | Mass (g) | m Mol | Mol % |
|---|---|---|---|
| TPPMS | 0.26 | 0.7 | 1.6 |
| DS | 13.31 | 28.6 | 64.3 |
| TS | 2.94 | 4.9 | 11.0 |
| ODS | 2.89 | 6.0 | 13.5 |
| OTS | 0.95 | 1.6 | 3.6 |
| SDS | 0.91 | 1.8 | 4.0 |
| STS | 0.52 | 0.9 | 2.0 |

Extraction of the sulfuric acid solution is carried out at constant temperature and with constant composition of the sulfonation mixture and for the same extraction time.

The following results are obtained:

TABLE 10

| Experiment | amine (g) | (m Mol) | toluene (g) | org. phase (g) | waste acid (g) |
|---|---|---|---|---|---|
| 1 | 9.1 | 26 | 36.4 | 50.9 | 426.6 |
| 2 | 15.2 | 43 | 60.8 | 84.3 | 423.7 |
| 3 | 21.3 | 60 | 85.2 | 123.6 | 414.9 |
| 4 | 27.4 | 78 | 109.6 | 156.4 | 412.6 |
| 5 | 30.5 | 86 | 122.0 | 172.9 | 411.6 |
| 6 | 33.5 | 95 | 134.0 | 192.3 | 407.2 |
| 7 | 39.6 | 112 | 158.4 | 221.0 | 409.0 |
| 8 | 45.7 | 129 | 182.8 | 257.0 | 403.3 |
| 9 | 51.8 | 147 | 207.2 | 288.0 | 402.7 |

The composition of the organic amine extraction solutions is given in the following table:

TABLE 11

| | Organic phase | | | | | | | | | | | |
|---|---|---|---|---|---|---|---|---|---|---|---|---|
| | sulfonation mixture 432 | | experiment 1 50.9 | | experiment 2 84.3 | | experiment 3 123.6 | | experiment 4 156.4 | | experiment 5 172.9 | |
| mass (g) composition | g | mMol | g | mMol | g | mMol | g | mMol | g | mMol | g | mMol |
| TPPMS | 0.26 | 0.7 | 0.20 | 0.5 | 0.19 | 0.5 | 0.20 | 0.5 | 0.25 | 0.7 | 0.24 | 0.7 |
| DS | 13.31 | 28.6 | 5.09 | 10.9 | 7.25 | 15.6 | 9.64 | 20.7 | 11.89 | 25.5 | 12.31 | 26.4 |
| TS | 2.94 | 4.9 | 0.28 | 0.5 | 0.73 | 1.2 | 1.74 | 2.9 | 2.86 | 4.7 | 2.94 | 4.9 |
| ODS | 2.89 | 6.0 | 1.71 | 3.5 | 2.11 | 4.4 | 2.52 | 5.2 | 2.70 | 5.6 | 2.71 | 5.6 |
| OTS | 0.95 | 1.6 | | | | | | | 0.20 | 0.3 | 0.41 | 0.7 |
| SDS | 0.91 | 1.8 | 0.55 | 1.1 | 0.56 | 1.1 | 0.63 | 1.3 | 0.61 | 1.2 | 0.59 | 1.2 |
| STS | 0.52 | 0.9 | 0.05 | 0.1 | 0.10 | 0.2 | 0.16 | 0.3 | 0.19 | 0.3 | 0.19 | 0.3 |
| Total | 21.78 | 44.5 | 7.88 | 16.6 | 10.94 | 23.0 | 14.89 | 30.9 | 18.70 | 38.3 | 19.39 | 39.8 |
| recovery percentage (1) total | | | 36% | | 50% | | 68% | | 86% | | 89% | |
| recovery percentage DS (2) | | | 38% | | 55% | | 72% | | 89% | | 93% | |
| recovery percentage TS (3) | | | 9.5% | | 25% | | 59% | | 97% | | 100% | |
| $SO_4^{2-}$ | | | 0.40% | | 0.42% | | 0.86% | | 1.40% | | 1.90% | |

| | sulfonation mixture 432 | | experiment 6 192.3 | | experiment 7 221.0 | | experiment 8 257.0 | | experiment 9 288.3 | |
|---|---|---|---|---|---|---|---|---|---|---|
| mass (g) composition | g | mMol | g | mMol | g | mMol | g | mMol | g | mMol |
| TPPMS | 0.26 | 0.7 | 0.24 | 0.7 | 0.24 | 0.7 | 0.25 | 0.7 | 0.26 | 0.7 |
| DS | 13.31 | 28.6 | 12.84 | 27.6 | 12.90 | 27.7 | 12.95 | 27.8 | 12.98 | 27.9 |
| TS | 2.94 | 4.9 | 2.87 | 4.8 | 2.92 | 4.8 | 2.95 | 4.9 | 2.93 | 4.9 |
| ODS | 2.89 | 6.0 | 2.93 | 6.1 | 2.86 | 5.9 | 2.86 | 5.9 | 2.86 | 5.9 |
| OTS | 0.95 | 1.6 | 0.60 | 1.0 | 0.62 | 1.1 | 0.81 | 1.4 | 0.84 | 1.4 |
| SDS | 0.91 | 1.8 | 0.67 | 1.4 | 0.62 | 1.3 | 0.70 | 1.4 | 0.72 | 1.5 |
| STS | 0.52 | 0.9 | 0.22 | 0.4 | 0.24 | 0.4 | 0.29 | 0.5 | 0.31 | 0.5 |
| Total | 21.78 | 44.5 | 20.37 | 42.0 | 20.40 | 41.9 | 20.81 | 42.6 | 20.90 | 42.8 |
| recovery percent- | | | 94% | | 94% | | 96% | | 96% | |

| | | | | |
|---|---|---|---|---|
| | TABLE 11-continued | | | |
| | Organic phase | | | |
| age (1) total | | | | |
| recovery percent- | 96% | 97% | 97% | 98% |
| age DS (2) | | | | |
| recovery percent- | 98% | 99% | 100% | 100% |
| age TS (3) | | | | |
| $SO_4^{2-}$ | 2.50% | 3.76% | 4.37% | 6.92% |

(1) extracted sulfonates based on total amount of sulfonates used (in weight %)
(2) extracted DS based on total amount of DS used (in weight %)
(3) extracted TS based on total amount of TS used (in weight %)

EXAMPLE 6

Influence of the amine quantity on the extraction of a sulfonation mixture containing TPPTS A sulfonation mixture, prepared as in Example 2 and containing primarily TPPTS, is extracted with different amounts of triisooctyl amine and toluene in the manner indicated in Example 5.

The sulfonation mixture (3911 g) exhibits the following composition:

TABLE 12

| | g | m Mol | Mol % |
|---|---|---|---|
| TPPDS | 29.9 | 64 | 17.3 |
| TS | 137.3 | 227 | 61.5 |
| ODS | 10.6 | 22 | 6.0 |
| OTS | 25.5 | 44 | 11.9 |
| STS | 7.0 | 12 | 3.3 |

Extraction of the sulfuric acid solution is carried out at 20° C. with constant composition of the sulfonation mixture and for the same extraction time. The results are compiled in the following table:

TABLE 13

| Experiment | amine (g) | (m Mol) | toluene (g) | org. phase (g) | waste acid (g) |
|---|---|---|---|---|---|
| 1 | 107 | 303 | 426 | 596 | 3848 |
| 2 | 177 | 501 | 708 | 1012 | 3784 |
| 3 | 248 | 703 | 993 | 1390 | 3762 |
| 4 | 320 | 907 | 1279 | 1787 | 3723 |
| 5 | 355 | 1006 | 1420 | 1977 | 3709 |
| 6 | 390 | 1105 | 1560 | 2165 | 3696 |
| 7 | 461 | 1306 | 1846 | 2541 | 3677 |
| 8 | 532 | 1507 | 2128 | 2927 | 3644 |

The organic phases are re-extracted according to Example 3 with the corresponding amounts of aqueous 7.1% potassium hydroxide solution. The compositions of the aqueous potassium salt solutions thus obtained are listed in the following table:

TABLE 14

| | Aqueous potassium salt solution | | | | | | | | | |
|---|---|---|---|---|---|---|---|---|---|---|
| | sulfonation mixture | | experiment 1 | | experiment 2 | | experiment 3 | | experiment 4 | |
| mass (g) | 3911 | | 402 | | 661 | | 925 | | 1219 | |
| composition | g | mMol | g | mMol | g | mMol | g | mMol | g | mMol |
| TPPDS | 29.9 | 64 | 12.4 | 27 | 14.9 | 32 | 20.1 | 43 | 26.9 | 58 |
| TS | 137.3 | 227 | 35.1 | 58 | 70.1 | 116 | 87.9 | 146 | 115.1 | 191 |
| ODS | 10.6 | 22 | 0.8 | 2 | 3.7 | 8 | 4.8 | 10 | 7.2 | 15 |
| OTS | 25.5 | 44 | 0.4 | 1 | 1.9 | 3 | 3.9 | 7 | 6.3 | 11 |
| STS | 7.0 | 12 | 3.7 | 6 | 3.9 | 7 | 4.9 | 8 | 5.7 | 10 |
| Total | 210.3 | 369 | 52.4 | 94 | 94.5 | 166 | 121.6 | 214 | 161.2 | 285 |
| recovery percentage (1) total | | | 25% | | 45% | | 58% | | 77% | |
| recovery percentage DS (2) | | | 41% | | 50% | | 67% | | 90% | |
| recovery percentage TS (3) | | | 26% | | 51% | | 64% | | 84% | |
| | sulfonation mixture | | experiment 5 | | experiment 6 | | experiment 7 | | experiment 8 | |
| mass (g) | 3911 | | 1345 | | 1484 | | 1788 | | 2104 | |
| composition | g | mMol | g | mMol | g | mMol | g | mMol | g | mMol |
| TPPDS | 29.9 | 64 | 28.7 | 62 | 28.9 | 62 | 29.0 | 62 | 28.9 | 62 |
| TS | 137.3 | 227 | 128.1 | 212 | 130.4 | 216 | 131.4 | 218 | 131.3 | 217 |
| ODS | 10.6 | 22 | 8.4 | 17 | 9.5 | 20 | 9.6 | 20 | 9.9 | 21 |
| OTS | 25.5 | 44 | 9.1 | 16 | 14.7 | 25 | 16.9 | 29 | 24.5 | 42 |
| STS | 7.0 | 12 | 6.4 | 11 | 6.8 | 11 | 6.8 | 11 | 6.8 | 11 |
| Total | 210.3 | 369 | 180.7 | 318 | 190.3 | 334 | 193.7 | 340 | 201.4 | 353 |
| recovery percentage (1) total | | | 86% | | 90% | | 92% | | 96% | |
| recovery percentage DS (2) | | | 96% | | 97% | | 97% | | 97% | |
| recovery percentage TS (3) | | | 93% | | 95% | | 96% | | 96% | |

(1) extracted sulfonates based on total amount of sulfonates used (in weight %)
(2) extracted DS based on total amount of DS used (in weight %)
(3) extracted TS based on total amount of TS used (in weight %)

EXAMPLE 7

Influence of the kind of amine used

A sulfonate mixture, prepared as in Example 1, is extracted with different amine/toluene mixtures in the usual manner. The composition of the feed sulfonation mixture as well as the extraction results are compiled in the following tables:

TABLE 15

| Composition of the sulfonation mixture (500 g) | | | |
|---|---|---|---|
| | g | m Mol | Mol % |
| TPPDS | 17.7 | 38 | 70.4 |
| TS | 4.2 | 7 | 13.0 |
| ODS | 3.4 | 7 | 13.0 |
| SDS | 0.95 | 2 | 3.6 |

TABLE 16

| sulfonation mixture (g) | feed amine | | toluene (g) | organic phase (g) | waste acid (g) |
|---|---|---|---|---|---|
| | | (g) | (mMol) | | |
| 500 | isotridecyl amine | 22.6 | 113 | 90.4 | 140.5 | 472.5 |
| 500 | di-(2-ethylhexyl) amine | 27.4 | 113 | 109.6 | 160.8 | 476.2 |
| 500 | diisotridecyl amine | 43.2 | 113 | 172.8 | 237.0 | 479.0 |
| 500 | diisononyl amine | 30.5 | 113 | 122.0 | 176.0 | 476.5 |
| 500 | tri-n-hexyl amine | 30.5 | 113 | 122.0 | 105.9 71.3 (2 phases) | 475.3 |
| 500 | tri-n-octyl amine | 40.1 | 113 | 160.4 | 225.8 | 474.7 |
| 500 | triisooctyl amine | 40.1 | 113 | 160.4 | 226.7 | 473.8 |
| 500 | triisononyl amine | 44.8 | 113 | 179.2 | 249.2 | 474.8 |
| 500 | tri-n-decyl amine | 49.6 | 113 | 198.4 | 271.1 | 474.9 |
| 500 | tribenzyl amine | 32.5 | 113 | 130.0 | solid | |

TABLE 17

| | composition of the organic phase | | | | | | | | composition of the waste acid phase | | | | | | | | $SO_4^{2-}$ content of the organic phase | |
|---|---|---|---|---|---|---|---|---|---|---|---|---|---|---|---|---|---|---|
| | DS | | TS | | ODS | | SDS | | DS | | TS | | ODS | | SDS | | | |
| | g | mMol | g | mMol | g | mMol | g | mMol | g | mMol | g | mMol | g | mMol | g | mMol | g | mMol |
| isotridecyl amine | 16.4 | 35 | 3.0 | 5 | 1.9 | 4 | 0.4 | 1 | 0.95 | 2 | 0.76 | 1 | 1.04 | 2 | | | 1.80 | 19 |
| di-(2-ethylhexyl)amine | 16.6 | 36 | 4.1 | 7 | 2.4 | 5 | 0.6 | 1 | | | | | 0.94 | 2 | | | 2.30 | 24 |
| di-isotridecyl amine | 16.6 | 35 | 3.2 | 5 | 1.9 | 4 | 0.92 | 2 | 0.52 | 1 | 0.29 | 1 | 1.52 | 3 | | | 1.54 | 16 |
| diisononyl amine | 17.4 | 37 | 4.0 | 7 | 2.5 | 5 | 0.74 | 1 | 0.38 | 1 | | | 0.95 | 2 | | | 1.36 | 14 |
| tri-n-hexyl amine (1) | 13.5 | 29 | 4.0 | 7 | 3.0 | 6 | 0.4 | 1 | | | | | 0.52 | 1 | | | 2.00 | 21 |
| tri-n-octyl amine | 17.3 | 37 | 4.1 | 7 | 2.4 | 5 | 0.86 | 2 | | | | | 1.09 | 2 | | | 2.37 | 25 |
| triisooctyl amine | 17.4 | 37 | 4.1 | 7 | 2.0 | 4 | 0.84 | 2 | | | | | 1.04 | 2 | | | 2.61 | 27 |
| triisononyl amine | 17.4 | 37 | 3.9 | 6 | 1.8 | 4 | 0.85 | 2 | | | | | 1.56 | 3 | | | 0.60 | 6 |
| tri-n-decyl amine | 17.5 | 38 | 4.0 | 7 | 1.9 | 4 | 0.87 | 2 | | | | | 1.04 | 2 | | | 2.49 | 26 |
| tribenzyl amine | turned solid when the amine/toluene mixture was added | | | | | | | | | | | | | | | | | |

(1) During extraction 3 phases occurred, whereby the upper phase still contained 0.32% (= 1 mMol) DS, the middle phase contained the majority of valuable product

We claim:

1. A process for the preparation of at least one of mono-, di-, and trisulfonated triaryl phosphine comprising sulfonating triaryl phosphines with oleum at 0° to 40° C. to form a sulfonation mixture, diluting said mixture with water to form an aqueous solution, extracting said aqueous solution with an organic solution of a water-insoluble amine in a water-insoluble organic solvent in an amount sufficient to deliver 0.5 to 1.5 mol of said amine per sulfonic acid group equivalent, separating said organic solution, mixing said organic solution with an aqueous solution of a base to form a basic aqueous phase, separating said basic aqueous phase and recovering at least one of said mono-, di-, and trisulfonated triaryl phosphine therefrom.

2. The process according to claim 1 wherein said organic solution is used in a sufficient amount to deliver 0.8 to 1.2 mols of said amine per sulfonic acid group equivalent.

3. The process according to claims 2 wherein said amine is open-chained, branched or unbranched, having 10 to 60 carbon atoms.

4. The process of claim 3 wherein said amine has 13 to 36 carbon atoms.

5. The process of claim 4 wherein said amine is isotridecyl amine, di-(2-ethylhexyl) amine, diisotridecyl amine, diisononyl amine, tri-n-hexyl amine, tri-n-octyl amine, triisocryl amine, triisononyl amine and tri-n-decyl amine.

6. The process according to claim 1 wherein said water-insoluble organic solvent is at least one of toluene and hydrocarbon fractions resembling kerosene.

7. The process according to claim 1, wherein said aqueous solution of a base is a solution of at least one of alkali hydroxide, ammonia, alkali carbonates, and water-soluble amines.

8. The process according to claim 1 further comprising the addition of said aqueous solution of a base in small amounts and separating said basic aqueous phase after each said addition.

9. The process of claim 1 wherein said aqueous solution of a base is added in a sufficient amount to provide a water soluble base in an amount chemically equivalent to said water-insoluble amine.

10. The process of claim 1 wherein said water is added to said mixture in a quantity sufficient to result in a sulfuric acid concentration of 0.5 to 50% by weight.

11. The process of claim 10 wherein said sulfuric acid concentration is 25–35% by weight.

* * * * *